United States Patent
Park et al.

(10) Patent No.: US 9,518,932 B2
(45) Date of Patent: Dec. 13, 2016

(54) METROLOGY OPTIMIZED INSPECTION

(71) Applicant: KLA-Tencor Corporation, Milpitas, CA (US)

(72) Inventors: Allen Park, San Jose, CA (US); Craig MacNaughton, Los Gatos, CA (US); Ellis Chang, Saratoga, CA (US)

(73) Assignee: KLA-Tencor Corp., Milpitas, CA (US)

( * ) Notice: Subject to any disclaimer, the term of this patent is extended or adjusted under 35 U.S.C. 154(b) by 39 days.

(21) Appl. No.: 14/517,751

(22) Filed: Oct. 17, 2014

(65) Prior Publication Data
US 2015/0124247 A1    May 7, 2015

Related U.S. Application Data

(60) Provisional application No. 61/900,869, filed on Nov. 6, 2013.

(51) Int. Cl.
| | |
|---|---|
| G01B 11/06 | (2006.01) |
| G01N 21/88 | (2006.01) |
| G03F 7/00 | (2006.01) |
| G01N 21/93 | (2006.01) |
| G01N 21/95 | (2006.01) |
| G01N 21/956 | (2006.01) |
| G03F 7/20 | (2006.01) |

(52) U.S. Cl.
CPC ............ *G01N 21/93* (2013.01); *G01B 11/0675* (2013.01); *G01N 21/9501* (2013.01); *G01N 21/956* (2013.01); *G03F 7/705* (2013.01); *G03F 7/70616* (2013.01); *G01B 11/06* (2013.01); *G01B 2210/56* (2013.01); *G01N 2201/061* (2013.01); *G01N 2201/105* (2013.01); *G01N 2201/11* (2013.01); *G01N 2201/125* (2013.01)

(58) Field of Classification Search
None
See application file for complete search history.

(56) References Cited

U.S. PATENT DOCUMENTS

| | | | | |
|---|---|---|---|---|
| 4,410,278 A | * | 10/1983 | Makihira | G01N 21/952 250/559.07 |
| 5,789,124 A | * | 8/1998 | Todd | G03F 7/26 382/145 |
| 5,838,450 A | * | 11/1998 | McCoy | G03F 7/70358 250/548 |
| 6,484,064 B1 | * | 11/2002 | Campbell | H01L 21/67276 438/14 |
| 6,552,337 B1 | * | 4/2003 | Cho | B82Y 35/00 257/E21.53 |

(Continued)

FOREIGN PATENT DOCUMENTS

JP    2009-210504    9/2009

OTHER PUBLICATIONS

International Search Report and Written Opinion for PCT/US2014/064103 mailed Feb. 16, 2015.

*Primary Examiner* — Tri Ton
*Assistant Examiner* — Jarreas C Underwood
(74) *Attorney, Agent, or Firm* — Ann Marie Mewherter

(57) ABSTRACT

Methods and systems for determining one or more parameters of a wafer inspection process are provided. One method includes acquiring metrology data for a wafer generated by a wafer metrology system. The method also includes determining one or more parameters of a wafer inspection process for the wafer or another wafer based on the metrology data.

37 Claims, 1 Drawing Sheet

(56) References Cited

U.S. PATENT DOCUMENTS

| | | | |
|---|---|---|---|
| 6,620,563 B2 * | 9/2003 | Maltabes | G03F 7/70633 430/22 |
| 6,630,996 B2 * | 10/2003 | Rao | G01N 21/9501 356/237.1 |
| 6,657,736 B1 * | 12/2003 | Finarov | G01B 11/24 356/237.5 |
| 6,781,688 B2 * | 8/2004 | Kren | G01N 21/9501 356/237.1 |
| 6,982,793 B1 * | 1/2006 | Yang | G03F 9/7076 356/401 |
| 7,001,830 B2 * | 2/2006 | Phan | G03F 7/70625 356/150 |
| 7,046,375 B2 * | 5/2006 | Bischoff | G03F 7/70625 250/559.22 |
| 7,321,426 B1 * | 1/2008 | Poslavsky | G01N 21/211 356/369 |
| 7,498,106 B2 * | 3/2009 | Mui | G03F 7/70625 156/345.24 |
| 7,502,121 B1 * | 3/2009 | Walecki | G01B 9/02021 356/479 |
| 7,526,354 B2 * | 4/2009 | Madriaga | G01B 11/14 700/98 |
| 7,646,906 B2 | 1/2010 | Saidin et al. | |
| 7,711,514 B2 | 5/2010 | Park et al. | |
| 7,801,635 B2 * | 9/2010 | Funk | G05B 19/41865 700/108 |
| 7,853,920 B2 * | 12/2010 | Preil | G03F 1/84 382/149 |
| 8,379,227 B2 * | 2/2013 | Naot | G01B 11/02 356/630 |
| 8,559,001 B2 | 10/2013 | Chang et al. | |
| 8,786,842 B2 | 7/2014 | Muller et al. | |
| 8,908,145 B2 * | 12/2014 | Shibazaki | G03F 7/70641 355/53 |
| 2005/0004774 A1 | 1/2005 | Marella et al. | |
| 2008/0094639 A1 | 4/2008 | Widmann et al. | |
| 2009/0290782 A1 | 11/2009 | Regensburger | |
| 2010/0060888 A1 | 3/2010 | Reich et al. | |
| 2011/0096339 A1 * | 4/2011 | Naot | G01B 11/02 356/630 |
| 2013/0310966 A1 | 11/2013 | MacNaughton et al. | |

\* cited by examiner

METROLOGY OPTIMIZED INSPECTION

BACKGROUND OF THE INVENTION

1. Field of the Invention

This invention generally relates to methods and systems for metrology optimized inspection in which metrology data for a wafer is used to alter one or more parameters of a wafer inspection process for the wafer or another wafer.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Many different types of inspection systems have adjustable output acquisition (e.g., data, signal, and/or image acquisition) and sensitivity (or defect detection) parameters such that different parameters can be used to detect different defects or avoid sources of unwanted (nuisance) events. Although an inspection system that has adjustable output acquisition and sensitivity parameters presents significant advantages to a semiconductor device manufacturer, these inspection systems are essentially useless if the incorrect output acquisition and sensitivity parameters are used for an inspection process. Although using the correct output acquisition and sensitivity parameters will have a dramatic effect on the results of inspection, it is conceivable that many inspection processes are currently being performed with incorrect or non-optimized output acquisition and sensitivity parameters.

In currently used methods for wafer inspection process setup, a defect engineer may set up a wafer inspection recipe with several limitations. For example, the user may set up the inspection sensitivity based on a limited number of wafers that are available and only selected areas on the wafers. A user also may choose to use multiple wafers to set up sensitivity in an effort to accommodate wafer-to-wafer variation due to fabrication process variability. In other applications, a user may choose data from one or more die to define reference (nominal) images for the purpose of setting up a reference die. In such applications, a user can guess the best place to collect data but that place may not represent true nominal conditions. In another application, a user may choose various defects for review sampling but the sampling population is based on die or locations where the noise level is often unknown.

In the area of inspection optimization, not knowing where the noisy areas are can result in setting up sensitivity based on only noisy regions or only quiet regions that may not truly reflect variations across wafers. If die row selection was done on a quiet region, additional nuisance defects may arise when additional wafers are scanned. If die selection was done in a noisy region, real defects may be missed during production wafer scans due to thresholds being set too high. With respect to nominal die selection, the challenge is to select dies that are at truly nominal conditions where average thickness, critical dimension (CD), etc. are present. Not having this data set can lead to selecting dies that do not represent the nominal signature. With regard to defect sampling, defects that are sampled in a noisy region can produce low signal-to-noise while an optimized sampling from a quiet region may yield more real defects.

Accordingly, it would be advantageous to develop systems and/or methods that do not have one or more of the disadvantages described above.

SUMMARY OF THE INVENTION

The following description of various embodiments is not to be construed in any way as limiting the subject matter of the appended claims.

One embodiment relates to a computer-implemented method for determining one or more parameters of a wafer inspection process. The method includes acquiring metrology data for a wafer generated by a wafer metrology system. The method also includes determining one or more parameters of a wafer inspection process for the wafer or another wafer based on the metrology data. The acquiring and determining steps are performed by a computer system.

The method described above may be performed as described further herein. In addition, the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for determining one or more parameters of a wafer inspection process. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to determine one or more parameters of a wafer inspection process. The system includes an inspection subsystem configured to generate output for a wafer. The system also includes a computer subsystem configured for performing the acquiring and determining steps of the method described above. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
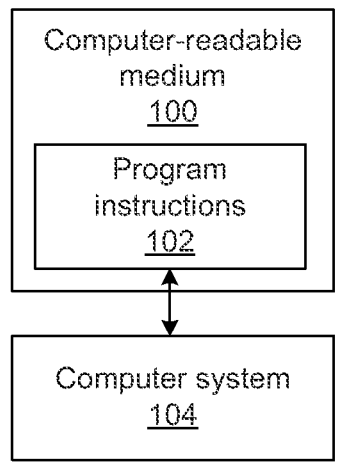
FIG. 1 is a block diagram illustrating one embodiment of a non-transitory computer-readable medium that includes program instructions executable on a computer system for performing one or more of the computer-implemented methods described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a computer-implemented method for determining one or more parameters of a wafer inspection process. The method includes acquiring metrology data for a wafer generated by a wafer metrology system. Acquiring the metrology data may include performing measurements on the wafer such as any of those described further herein using a wafer metrology tool, which may be configured as described herein. In this manner, acquiring the metrology data may include measuring the wafer. However, acquiring the metrology data does not necessarily include performing measurements of the wafer. For example, acquiring the metrology data may include acquiring the metrology data from a storage medium in which the metrology data has been stored (e.g., by the metrology system). Acquiring the metrology data from the storage medium may be performed in any suitable manner, and the storage medium from which the metrology data is acquired may include any of the storage media described herein.

In one embodiment, the metrology data includes information for warp of the wafer. In another embodiment, the metrology data includes information for bow of the wafer. In an additional embodiment, the metrology data includes a thickness of a film formed on the wafer. In a further embodiment, the metrology data includes a critical dimension (CD) of a patterned structure formed on the wafer. In some embodiments, the metrology data includes more than two million metrology data points generated across the wafer. For example, relatively high resolution metrology points (i.e., millions of metrology data points acquired across a wafer) can be used to identify potential sources of inspection noise for recipe setup. The metrology data described above may be generated by any suitable metrology tool in any suitable manner.

With ever shrinking process windows and relatively large wafer diameters, a relatively small change in wafer bow and warp can have a significant effect on film thickness and CD variation. In inspection, often defect data can be inundated with nuisance defects due to such variations but has never been compensated for. By metrology-aware inspection described herein, parameter(s) of wafer inspection such as inspection sensitivity and/or die sampling may be optimized as described further herein.

The method includes determining one or more parameters of a wafer inspection process for the wafer or another wafer based on the metrology data. For example, metrology data described herein (e.g., mask metrology, wafer film thickness, wafer CD metrology) can be linked to inspection as described herein. In this manner, the metrology data may be fed forward to inspection. For example, a metrology tool such as one of those described herein can be configured to send metrology data for a wafer directly to an inspection system. The inspection system may then use the metrology data to perform one or more steps of the methods described herein such as recipe setup and/or defect sampling, which may be performed as described further herein.

In this manner, metrology data can be integrated into inspection to fine tune inspection and defect sampling. In one such example, data may be sent from a metrology system to inspection where inspection uses data to classify and/or group areas based on variation in the metrology data. Once the noisy and quiet areas are identified, an inspection strategy can be set accordingly. As such, the embodiments described herein are configured for metrology optimized inspection (e.g., inspection having improved detection sensitivity and improved defect analysis based on metrology data). In this manner, metrology data such as wafer bow, warp, and thickness data can be used to improve inspection. The interaction of wafer metrology and inspection can help set up production worthy inspection processes while prioritizing potential real defects.

In one embodiment, the one or more parameters of the wafer inspection process that are determined for one or more areas on the wafer or the other wafer are different from the one or more parameters determined for one or more other areas on the wafer or the other wafer. For example, based on variations in the metrology data across the wafer (i.e., as a function of position or region on the wafer), the parameter(s) of the wafer inspection process can be set to vary across the wafer. In one such example, based on metrology data for an edge region of the wafer, an edge yield inspection strategy can be defined. In addition, the metrology data may indicate that different regions of the wafer proximate to the edge of the wafer may have different issues. Therefore, different inspection strategies can be implemented for different edge regions based on the potential yield issues that may be present in the different edge regions, which can be determined based on the metrology data. The variations in the metrology data across the wafer can also be used to determine different regions on the wafer having similar metrology data. The regions having similar metrology data (e.g., noisy regions or quiet regions) can then be grouped together or assigned the same classification. Regions in the same group or having the same assigned classification can then be assigned the same inspection process parameter(s). In this manner, the wafer inspection process can be optimized based on variations in the metrology data.

In some embodiments, the one or more parameters of the wafer inspection process include one or more parameters of defect detection performed during the wafer inspection process. In this manner, the embodiments described herein can be used to improve defect detection by integrating metrology data from wafer measurement. The one or more parameters of defect detection may include any parameters of inspection system output processing (i.e., signal, image, or data processing) and any parameter(s) of any defect detection algorithm(s) and/or method(s) performed to detect defects on the wafer. For instance, as described further herein, the one or more parameters may include a sensitivity of the inspection or defect detection. However, any other parameter(s) of defect detection may be altered in a similar manner including a complete change in defect detection algorithm and/or method.

In another embodiment, the one or more parameters of the wafer inspection process include one or more parameters that at least partially determine a sensitivity of defect detection performed for one or more areas of the wafer or the other wafer. In this manner, metrology data can be linked to inspection for recipe sensitivity. For example, wafer geometry and metrology can be used to optimize inspection sensitivity and to locate noisy/quiet regions for improved data analysis. By linking metrology and inspection technologies, the embodiments described herein can deliver a unique solution in providing the most sensitive inspections. In addition, the embodiments described herein can help explain when there are relatively large amounts of nuisance defects and allow a user to determine how to address it. In this manner, the close connectivity of metrology and inspection described herein can be leveraged to provide the most advanced inspection. The embodiments described herein also provide additional use cases and therefore additional value for metrology tools.

In an additional embodiment, the one or more parameters of the wafer inspection process include one or more parameters of defect sampling performed during the wafer inspection process. For example, the metrology-aware inspection described herein can provide clues to tune sampling so that real defects are likely to be selected for defect review (e.g., scanning electron microscope (SEM) review). In addition, the metrology data described herein can be used for predicting where nuisance defects may occur and therefore adjusting review sampling and predicting noise. In this manner, metrology data can be linked to inspection for review sample binning. As such, the embodiments described herein can be used to improve defect sampling by integrating metrology data from wafer measurement.

In one embodiment, the one or more parameters of the wafer inspection process include a selection of one or more areas on the wafer or the other wafer at which output is generated by a wafer inspection system during the wafer inspection process. For example, metrology data described herein may be linked to inspection to automatically determine die selection for recipe optimization and review sampling. In addition, a good variety of quiet and noisy areas can be selected to optimize a production quality recipe. Furthermore, the metrology data described herein can be used to separate critical inspection and metrology regions such that inspection can be performed where the signal is higher for defects of interest (DOIs) on the wafer.

In some embodiments, determining the one or more parameters includes determining a probability of CD variation in one or more areas of the wafer or the other wafer based on the metrology data, determining at least one of the one or more areas in which the probability is higher than other of the one or more areas, and determining the one or more parameters such that the at least one of the one or more areas is sampled by a wafer inspection system that performs the wafer inspection process more heavily than the other of the one or more areas. The probability of CD variation in different areas of the wafer may be determined in any suitable manner. For instance, if there is a bow or warp in the wafer, some portions of the wafer may be out of focus in a lithography step performed on the wafer and therefore may have CDs that vary from the designed CDs. Therefore, based on information about the wafer determined from the metrology data, areas of the wafer that may have relatively high CD variation can be determined and then sampled more heavily than areas that will not likely have high CD variations. In this manner, metrology data such as that described herein can be used to tune inspection sampling to look for possible CD variation. As such, the metrology data described herein can be used to separate critical inspection and metrology regions such that areas on the wafer where variations may be high are measured.

In another embodiment, determining the one or more parameters includes selecting one or more die on the wafer or the other wafer based on the metrology data, acquiring output generated by a wafer inspection system for the one or more selected die, and generating a reference die from the output generated by the wafer inspection system for the one or more die. The reference die is used in the wafer inspection process to detect defects on the wafer or the other wafer. For example, the metrology data described herein can be used to identify a nominal condition area on the wafer, and then a set of reference die (i.e., one or more reference dies) may be selected from that area. By selecting die(s) in a quiet region of a wafer, the quality of the nominal image can be improved. In addition, the film thickness and CD metrology data can be used to identify a set of dies that are representative of nominal conditions. As such, the metrology data described herein can be used to identify location(s) of nominal image(s) for reference image selection to enhance die-to-reference image inspection. In this manner, metrology data can be linked to inspection for reference die selection.

In a further embodiment, determining the one or more parameters of the wafer inspection process includes determining, based on one or more first parameters of the wafer inspection process and the metrology data, which one or more areas on the wafer or the other wafer will produce more noise than other areas on the wafer or the other wafer in the wafer inspection process and which one or more additional areas on the wafer or the other wafer will produce less noise than other areas on the wafer or the other wafer and determining one or more second parameters of the wafer inspection process based on the one or more areas and the one or more additional areas. For example, metrology data such as wafer warp or bow data collection can be used to determine locations on a wafer where an inspection recipe is optimized. By utilizing millions of data points and identifying regions that are noisy versus quiet, wafer inspection parameter(s) such as recipe sensitivity setting and defect sampling can be optimized based on foreknowledge of the quality of the region. For example, the metrology data described herein can help understand the amount of variation in the wafer to anticipate variation to set inspection sensitivity accordingly. In one such example, the metrology data can be used to separate noisy and nominal areas and to set inspection sensitivity independently for the different areas. In addition, the metrology data can be used to identify noisy inspection area(s) for nuisance data prioritization and filtering. For example, significantly more nuisance defects will typically be detected in a high noise region on the wafer, which can be determined from the metrology data as described herein, than a region having nominal or less noise. On the other hand, in relatively low noise regions, there is a higher probability of detecting real defects. Therefore, one or more parameters of nuisance filtering can be determined based on the expected noise in different regions of the wafer.

In one such embodiment, the one or more second parameters include one or more defect sampling parameters, and the one or more defect sampling parameters are determined to preferentially select random defects in the one or more additional areas that will produce less noise than the other areas. For example, by sampling defects from relatively quiet regions on the wafer, sampling of defects can show more random defects. In this manner, quiet regions may be selected for random defect discovery. In addition, review sampling can be skewed toward quiet regions on the wafer to increase the chance of selecting real defects.

In another such embodiment, the one or more second parameters include one or more defect sampling parameters, and the one or more defect sampling parameters are determined to preferentially select systematic defects in the one or more areas that will produce more noise than the other areas. For example, noisy regions may be a good proxy for sampling potential systematic defects.

In both of the embodiments described above, the defects that are detected in the wafer inspection process may be assigned an ID that identifies the high/low variation region in which the defects were detected. In other words, defects detected in a region having a high variation in the metrology data may be assigned one ID, and defects detected in a region having a low variation in the metrology data may be assigned a different ID. In this manner, the defects may be sampled and classified by regions in which they were detected. The defect detection results of the wafer inspection process may be correlated to the metrology data in any other suitable manner. For example, a defect map generated by inspection may be correlated to a metrology map.

In one embodiment, the method includes acquiring metrology or inspection data for a reticle, the reticle is used to print patterned features on the wafer, and determining the one or more parameters of the wafer inspection process is performed based on the metrology data for the wafer in combination with the metrology or inspection data for the reticle. In this manner, mask metrology data may be used to identify within reticle anomalies that may contribute to inspection noise. For example, information about defects or potential defects detected on a reticle by reticle metrology and/or inspection can be used to determine information about defects or potential defects that will be printed on a wafer by that reticle. In some such instances, information about the defects on the reticle that are determined to be permissible by reticle inspection and/or metrology may be used to identify locations on the wafer where those permissible defects will be located. Those locations may be scanned and checked for defects in wafer inspection to ensure that the defects are actually permissible. Alternatively, those locations may not be inspected at all since presumably if wafer defects are detected there, those wafer defects will be permissible as a result of the permissible reticle defects. Therefore, the one or more parameters of the wafer inspection process that are determined based, at least in part, on the metrology or inspection data for the reticle may include where to inspect on the wafer, types of inspection, classifications to be assigned to defects detected in certain areas of the wafer, etc. The reticle inspection and/or metrology data can be used in combination with the wafer metrology data for determining wafer inspection parameter(s) in a number of different ways such as via a set of rules that define suitable wafer inspection parameter(s) for different combinations of reticle inspection and/or metrology data and wafer metrology data. In addition, the wafer inspection parameter(s) can be defined based on the reticle inspection and/or metrology data as described in U.S. Patent Application Publication No. 2005/0004774 by Marella et al. published on Jan. 6, 2005, which is incorporated by reference as if fully set forth herein. The embodiments described herein may be further configured as described in this patent application.

In a similar manner, information about "defects" in design data may be used to determine the one or more parameters of the wafer inspection process in combination with the wafer metrology data (and possibly the reticle inspection and/or metrology data). Information about the "defects" in the design data may be acquired using methods and systems such as those described in U.S. Pat. No. 7,646,906 issued to Saidin et al. on Jan. 12, 2010, which is incorporated by reference as if fully set forth herein. The embodiments described herein may be further configured as described in this patent.

In some embodiments, the one or more parameters include one or more areas of the wafer or the other wafer used for field-to-field inspection performed within dies during the wafer inspection process. In this manner, the metrology data described herein may be used to define areas on a wafer that are suitable for field-to-field inspection within die. For example, the metrology data can be used to define one or more high noise regions on the wafer in which field-to-field inspection should be performed. In particular, in relatively high noise regions, the noise variation from die-to-die may be much greater than the noise variation from field-to-field. Therefore, in relatively high noise regions, die-to-die detection may result in the detection of significantly more nuisance defects than field-to-field detection. As such, parameter(s) of the wafer inspection process can be set such that the type of detection (e.g., die-to-die or field-to-field) that is performed is varied depending on the noise that is expected in different regions of the wafer.

In another embodiment, the method includes determining one or more parameters of a fabrication process for the wafer or the other wafer based on the metrology data, the wafer inspection process is performed on the wafer or the other wafer after the fabrication process is performed on the wafer or the other wafer, and determining the one or more parameters of the wafer inspection process is performed based on the metrology data for the wafer in combination with the one or more parameters of the fabrication process. In some such embodiments, the fabrication process may be an etch process. However, the fabrication process may be any other fabrication process that can be performed on the wafer. In addition, the fabrication process that is performed on the wafer or other wafer may include one or more fabrication process steps (e.g., an etch process step possibly with one or more other process steps). In one such example, the metrology data described herein such as within wafer field variation data can be used to optimize one or more etch conditions and to use the combined data to optimize inspection of the wafer.

In additional embodiments, determining the one or more parameters includes determining one or more characteristics of noise in output generated for one or more areas of the wafer or the other wafer by a wafer inspection system during the wafer inspection process based on the metrology data and determining one or more parameters of output noise reduction performed during the wafer inspection process based on the one or more determined characteristics of the noise. Therefore, the embodiments described herein may be configured for dynamic noise detection for inspection. For example, the metrology data described herein can be used for determination of high and low frequency noise, which can then be used to determine appropriate noise reduction technologies.

The acquiring and determining steps described herein are performed by a computer system, which may be configured as described further herein.

As will be clear from the description of the embodiments provided herein, the embodiments of the invention have a number of advantages over current methods and systems for setting up wafer inspection recipes. For example, manually examining metrology data may help a user to pick regions on a wafer for inspection, but it would be time consuming and ineffective. There are currently no direct links between metrology and inspection and, therefore, use of external data sources such as mask metrology, film thickness, and CD metrology would not only be difficult to do but also leaves plenty of room for error. Linking the metrology data with an inspection recipe to automatically tune the recipe and review sampling can make this flow efficient and production worthy.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

An additional embodiment relates to a non-transitory computer-readable medium storing program instructions executable on a computer system for performing a computer-implemented method for determining one or more parameters of a wafer inspection process. One such embodiment is shown in FIG. 1. In particular, as shown in FIG. 1, computer-readable medium 100 includes program instructions 102 executable on computer system 104. The computer-implemented method includes the steps of the method described above. The computer-implemented method for which the program instructions are executable may include any other step(s) described herein.

Program instructions 102 implementing methods such as those described herein may be stored on computer-readable medium 100. The computer-readable medium may be a storage medium such as a magnetic or optical disk, or a magnetic tape or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 2:
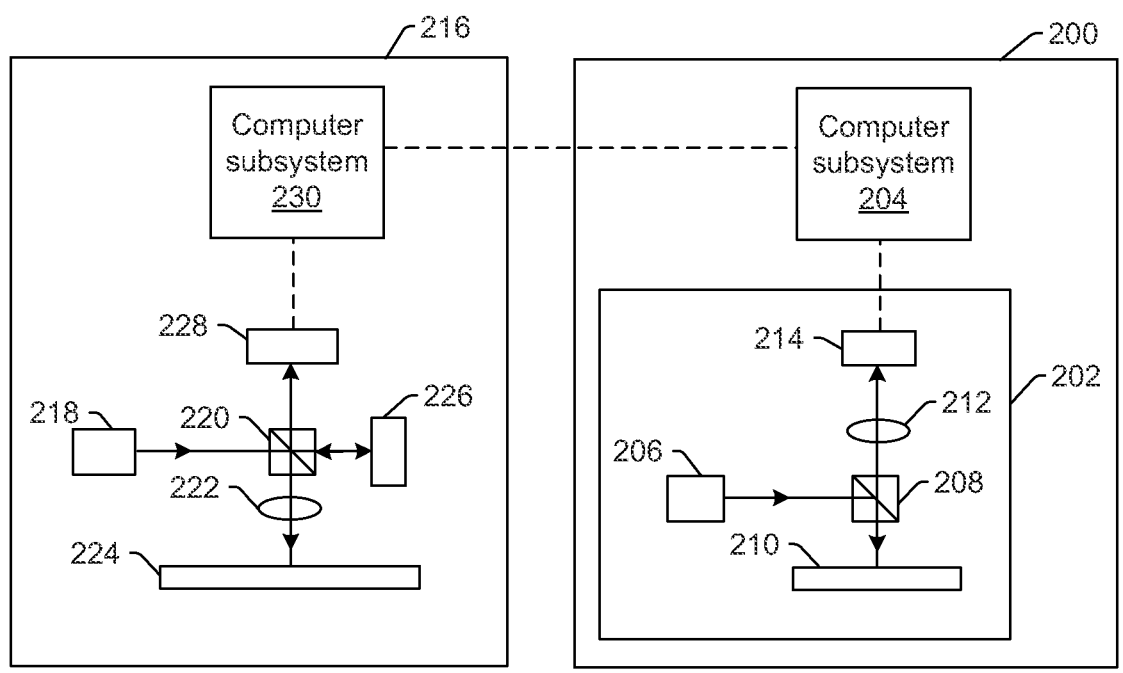
FIG. 2 is a schematic diagram illustrating a side view of one embodiment of a system configured to determine one or more parameters of a wafer inspection process.

An additional embodiment relates to a system configured to determine one or more parameters of a wafer inspection process. One embodiment of such a system is shown in FIG. 2. System 200 includes inspection subsystem 202 configured to generate output for a wafer, which is configured in this embodiment as described further herein. The system also includes computer subsystem 204 configured for performing the acquiring and determining steps described herein. The computer subsystem may be configured to perform these steps according to any of the embodiments described herein. The computer subsystem and the system may be configured to perform any other step(s) described herein and may be further configured as described herein.

The inspection subsystem may be configured to generate the output for the wafer by scanning the wafer with light and detecting light from the wafer during the scanning. For example, as shown in FIG. 2, the inspection subsystem includes light source 206, which may include any suitable light source known in the art. Light from the light source may be directed to beam splitter 208, which may be configured to direct the light from the light source to wafer 210. The light source may be coupled to any other suitable elements (not shown) such as one or more condensing lenses, collimating lenses, relay lenses, objective lenses, apertures, spectral filters, polarizing components and the like. As shown in FIG. 2, the light may be directed to the wafer at a normal angle of incidence. However, the light may be directed to the wafer at any suitable angle of incidence including near normal and oblique incidence. In addition, the light or multiple light beams may be directed to the wafer at more than one angle of incidence sequentially or simultaneously. The inspection subsystem may be configured to scan the light over the wafer in any suitable manner.

Light from wafer 210 may be collected and detected by one or more channels of the inspection subsystem during scanning. For example, light reflected from wafer 210 at angles relatively close to normal (i.e., specularly reflected light when the incidence is normal) may pass through beam splitter 208 to lens 212. Lens 212 may include a refractive optical element as shown in FIG. 2. In addition, lens 212 may include one or more refractive optical elements and/or one or more reflective optical elements. Light collected by lens 212 may be focused to detector 214. Detector 214 may include any suitable detector known in the art such as a charge coupled device (CCD) or another type of imaging detector. Detector 214 is configured to generate output that is responsive to the reflected light collected by lens 212. Therefore, lens 212 and detector 214 form one channel of the inspection subsystem. This channel of the inspection subsystem may include any other suitable optical components (not shown) known in the art.

Since the inspection subsystem shown in FIG. 2 is configured to detect light specularly reflected from the wafer, the inspection subsystem is configured as a bright field (BF) inspection subsystem. Such an inspection subsystem may, however, also be configured for other types of wafer inspection. For example, the inspection subsystem shown in FIG. 2 may also include one or more other channels (not shown). The other channel(s) may include any of the optical components described herein such as a lens and a detector, configured as a scattered light channel. The lens and the detector may be further configured as described herein. In this manner, the inspection subsystem may also be configured for dark field (DF) inspection.

Computer subsystem 204 is coupled to the inspection subsystem such that output generated by the detector(s) during scanning may be provided to computer subsystem 204. For example, the computer subsystem may be coupled to detector 214 (e.g., by one or more transmission media shown by the dashed line in FIG. 2, which may include any suitable transmission media known in the art) such that the computer subsystem may receive the output generated by the detector.

The computer subsystem may be configured to perform any step(s) described herein. For example, computer subsystem 204 may be configured for performing the acquiring and determining steps as described herein. In addition, computer subsystem 204 may be configured to perform any other steps described herein. The computer subsystem may also be configured to perform one or more steps of a wafer inspection process based on the one or more parameters described herein. For instance, any defect detection, defect sampling, etc. performed by the computer subsystem may be performed according to any parameter(s) determined by the embodiments described herein.

In some embodiments, the systems described herein may include, or may simply be coupled to, a metrology system. For example, as will be described further herein, a computer subsystem of an inspection system such as that described above may be coupled to a computer subsystem of a metrology system such that the computer subsystem of the inspection system can receive metrology data from the computer subsystem of the metrology system.

One embodiment of a metrology system that can generate the metrology data described herein is shown in FIG. 2. In this embodiment, metrology system 216 includes light source 218 that is configured to generate light that is directed from the light source to beam splitter 220. The beam splitter is configured to reflect one portion of the light from the light source to refractive optical element 222 that focuses that portion of the light to wafer 224. The beam splitter is also configured to transmit another portion of the light from the light source to reflective optical element 226 that serves as a reference in the metrology system. The light reflected from the wafer that passes through the refractive optical element and the light reflected from the reflective optical element may be combined by the beam splitter and directed to detector 228. In this manner, the two reflected beams (one from the wafer and the other from the reference) may interfere with each other, and the resulting interference may be detected by the detector. As such, the metrology system shown in FIG. 2 is configured as an interferometer. Computer subsystem 230 may be coupled to the detector as described herein such that the computer subsystem can receive output generated by the detector and determine one or more characteristics of the wafer (i.e., the metrology data) from the received output. The metrology data determined in this manner may include any of the metrology data described herein and may be determined in any suitable manner known in the art.

Although the metrology system is shown in FIG. 2 as an interferometer, any metrology system included in, or coupled to, the systems described herein may have any other suitable configuration known in the art. For example, the metrology system may also or alternatively be configured as a scatterometer, a reflectometer, an ellipsometer, a diffractometer, or some combination or variation thereof. The metrology system may also be further configured as described in U.S. Pat. No. 7,711,514 issued to Park et al. on May 4, 2010, U.S. Pat. No. 8,559,001 issued to Chang et al. on Oct. 15, 2013, and U.S. Pat. No. 8,786,842 issued to Muller et al. on Jul. 22, 2014, and U.S. Patent Application Publication No. 2013/0310966 by MacNaughton et al. published Nov. 21, 2013, all of which are incorporated by reference as if fully set forth herein. The embodiments described herein may be further configured as described in these patents and patent application.

Computer subsystems 204 and 230 may be coupled by one or more transmission media shown by the dashed line between the computer subsystems in FIG. 2. In this manner, the two computer subsystems may send and receive information to and from each other. As such, the metrology data may be fed forward to an inspection system by a metrology system. However, the metrology data may also be stored in a storage medium such as that described and shown further herein by the metrology system, and then the computer subsystem of the inspection system can retrieve the metrology data from that storage medium.

It is noted that FIG. 2 is provided herein to generally illustrate a configuration of an inspection system and a metrology system that may be included in the system embodiments described herein. Obviously, the inspection and metrology system configurations described herein may be altered to optimize the performance of the inspection system and metrology system as is normally performed when designing commercial inspection and metrology systems. In addition, the systems described herein may be implemented using an existing inspection system and/or existing metrology system (e.g., by adding functionality described herein to an existing inspection or metrology system) such as the 29xx/28xx series of wafer inspection tools and the WaferSight PWG metrology tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, methods and systems for determining one or more parameters of a wafer inspection process are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for determining one or more parameters of a wafer inspection process, comprising:

acquiring metrology data for a wafer generated by a wafer metrology system, wherein the wafer metrology system performs measurements on the wafer thereby generating the metrology data, and wherein acquiring the metrology data comprises acquiring the metrology data from a storage medium in which the metrology data has been stored by the wafer metrology system;and determining one or more parameters of a wafer inspection process for the wafer or another wafer based on the metrology data, wherein said acquiring and said determining are performed by a computer system, wherein the computer system comprises one or more processors and executes instructions from a memory medium, wherein the wafer inspection process is performed to detect defects on the wafer or the other wafer, and wherein determining the one or more parameters comprises:

determinining a probability of critical dimension variation in one or more areas of the wafer or the other wafer based on the metrology data;

determining at least one of the one or more areas in which the probability is higher than other of the one or more areas; and determining the one or more parameters such that the at least one of the one or more areas is sampled by a wafer inspection system that performs the wafer inspection process more heavily than the other of the one or more areas.

2. The method of claim 1, Wherein the metrology data comprises information for warp of the wafer.

3. The method of claim 1, wherein the metrology data comprises information for bow of the wafer.

4. The method of claim 1, wherein the metrology data comprises a thickness of a film formed on the wafer.

5. The method of claim 1, wherein the metrology data comprises a critical dimension of a patterned structure formed on the wafer.

6. The method of claim 1, wherein the one or more parameters of the wafer inspection process that are determined for the one or more areas on the wafer or the other wafer are different from the one or more parameters determined for one or more other areas on the wafer or the other wafer.

7. The method of claim 1, wherein the one or more parameters of the wafer inspection process comprise one or more parameters of defect detection performed during the wafer inspection process.

8. The method of claim 1, wherein the one or more parameters of the wafer inspection process comprise one or more parameters that at least partially determine a sensitivity of defect detection performed for the one or more areas of the wafer or the other wafer.

9. The method of claim 1, wherein the one or more parameters of the wafer inspection process comprise one or more parameters of defect sampling performed during the wafer inspection process.

10. The method of claim 1, wherein the one or more parameters of the wafer inspection process comprise a selection of the one or more areas on the wafer or the other wafer at which output is generated by the wafer inspection system during the wafer inspection process.

11. The method of claim 1, wherein determining the one or more parameters further comprises:

selecting one or more die on the wafer or the other wafer based on the metrology data;

acquiring output generated by the wafer inspection system for the e or more selected die; and generating a reference die from the output generated by the wafer inspection system for the one or more selected die, wherein the reference die is used in the wafer inspection process to detect the defects on the wafer or the other wafer.

12. The method of claim 1, wherein determining the one or more parameters of the wafer inspection process further comprises:

determining, based on one or more first parameters of the wafer inspection process and the metrology data, which one or more areas on the wafer or the other wafer will produce more noise than other areas on the wafer or the other wafer in the wafer inspection process and which one or more additional areas on the wafer or the other wafer will produce less noise than other areas on the wafer or the other wafer; and determining one or more second parameters of the wafer inspection process based on the one or more areas that will produce more noise than the other areas and the one or more additional areas.

13. The method of claim 12, wherein the one or more second parameters comprise one or more defect sampling parameters, and wherein the one or more defect sampling parameters are determined to preferentially select random defects in the one or more additional areas that will produce less noise than the other areas.

14. The method of claim 12, wherein the one or more second parameters comprise one or more defect sampling parameters, and wherein the one or more defect sampling parameters are determined to preferentially select systematic defects in the one or more areas that will produce more noise than the other areas.

15. The method of claim 1, further comprising acquiring metrology or inspection data for a reticle, wherein the reticle is used to print patterned features on the wafer, and wherein determining the one or more parameters of the wafer inspection process is performed based on the metrology data for the wafer in combination with the metrology or inspection data for the reticle.

16. The method of claim 1, wherein the one or more parameters comprise one or more additional areas of the wafer or the other wafer used for field-to-field inspection performed within dies during the wafer inspection process.

17. The method of claim 1, further comprising determining one or more parameters of a fabrication process for the wafer or the other wafer based on the metrology data, wherein the wafer inspection process is further performed on the wafer or the other wafer after the fabrication process is performed on the wafer or the other wafer, and wherein determining the one or more parameters of the wafer inspection process is performed based on the metrology data for the wafer in combination with the one or more parameters of the fabrication process.

18. The method of claim 1, wherein determining the one or more parameters further comprises determining one or more characteristics of noise in output generated for one or more additional areas of the wafer or the other wafer by the wafer inspection system during the wafer inspection process based on the metrology data and determining one or more parameters of output noise reduction performed during the wafer inspection process based on the one or more determined characteristics of the noise.

19. A non-transitory computer-readable medium, storing program instructions executable on a computer system for performing a computer-implemented method for determining one or more parameters of a wafer inspection process, wherein the computer-implemented method comprises:

acquiring metrology data for a wafer generated by a wafer metrology system, wherein the wafer metrology system performs measurements on the wafer thereby generating the metrology data, and wherein acquiring the metrology data comprises acquiring the metrology data from a storage medium in which the metrology data has been stored by the wafer metrology system; and determining one or more parameters of a wafer inspection process for the wafer or another wafer based on the metrology data, wherein the computer system comprises one or more processors and executes the program instructions from the non-transitory computer-readable medium, wherein the wafer inspection process is performed to detect defects on the wafer or the other wafer, and wherein determining the one or more parameters comprises:

determining a probability of critical dimension variation in one or more areas of the wafer or the other wafer based on the metrology data;

determining at least one of the one or more areas in which the probability is higher than other of the one or more areas; and determining the one or more parameters such that the at least one of the one or more areas is sampled by a wafer inspection system that performs the wafer inspection process more heavily than the other of the one or more areas.

20. A system configured to determine one or more parameters of a wafer inspection process, comprising:

an inspection subsystem configured to generate output for a wafer by scanning a wafer with light and detecting light from the wafer during the scanning, wherein the inspection subsystem comprises at least a light source and a detector, and wherein the inspection subsystem scans light from the light source over the wafer, and wherein the detector detects the light from the wafer during the scanning; and a computer subsystem configured for:

acquiring metrology data for the wafer generated by a wafer metrology system, wherein the wafer metrology system performs measurements on the wafer thereby generating the metrology data, and wherein acquiring the metrology data comprises acquiring the metrology data from a storage medium in which the metrology data has been stored by the wafer metrology system; and determining one or more parameters of a wafer inspection process for the wafer or another wafer based on the metrology data, wherein the computer subsystem comprises one or more processors and executes instructions from a memory medium, wherein the wafer inspection process is performed with the inspection subsystem and the one or more determined parameters to detect defects on the wafer or the other wafer, and wherein determining the one or more parameters comprises:

determining a probability of critical dimension variation in one or more areas of the wafer or the other wafer based on the metrology data;

determining at least one of the one or more areas in which the probability is higher than other of the one or more areas; and determining the one or more parameters such that the at least one of the one or more areas is sampled by the inspection subsystem that performs the wafer inspection process more heavily than the other of the one or more areas.

21. The system of claim 20, wherein the metrology data comprises information for warp of the wafer.

22. The system of claim 20, wherein the metrology data comprises information for bow of the wafer.

23. The system of claim 20, wherein the metrology data comprises a thickness of a film formed on the wafer.

24. The system of claim 20, wherein the metrology data comprises a critical dimension of a patterned structure formed on the wafer.

25. The system of claim 20, wherein the one or more parameters of the wafer inspection process that are determined for the one or more areas on the wafer or the other wafer are different from the one or more parameters determined for one or more other areas on the wafer or the other wafer.

26. The system of claim 20, wherein the one or more parameters of the wafer inspection process comprise one or more parameters of defect detection performed during the wafer inspection process.

27. The system of claim 20, wherein the one or more parameters of the wafer inspection process comprise one or more parameters that at least partially determine a sensitivity of defect detection performed for the one or more areas of the wafer or the other wafer.

28. The system of claim 20, wherein the one or more parameters of the wafer inspection process comprise one or more parameters of defect sampling performed during the wafer inspection process.

29. The system of claim 20, wherein the one or more parameters of the wafer inspection process comprise a selection of the one or more areas on the wafer or the other wafer at which output is generated by the inspection subsystem during the wafer inspection process.

30. The system of claim 20, wherein determining the one or more parameters further comprises:

selecting one or more die on the wafer or the other wafer based on the metrology data;

acquiring output generated by the inspection subsystem for the one or more selected die; and generating a reference die from the output generated by the inspection subsystem for the one or more selected die, wherein the reference die is used in the wafer inspection process to detect the defects on the wafer or the other wafer.

31. The system of claim 20, wherein determining the one or more parameters of the wafer inspection process further comprises:

determining, based on one or more first parameters of the wafer inspection process and the metrology data, which one or more areas on the wafer or the other wafer will produce more noise than other areas on the wafer or the other wafer in the wafer inspection process and which one or more additional areas on the wafer or the other wafer will produce less noise than other areas on the wafer or the other wafer; and determining one or more second parameters of the wafer inspection process based on the one or more areas that will produce more noise than the other areas and the one or more additional areas.

32. The system of claim 31, wherein the one or more second parameters comprise one or more defect sampling parameters, and wherein the one or more defect sampling parameters are determined to preferentially select random defects in the one or more additional areas that will produce less noise than the other areas.

33. The system of claim 31, wherein the one or more second parameters comprise one or more defect sampling parameters, and wherein the one or more defect sampling parameters are determined to preferentially select systematic defects in the one or more areas that will produce more noise than the other areas.

34. The system of claim 20, wherein the computer subsystem is further configured for acquiring metrology or inspection data for a reticle, wherein the reticle is used to print patterned features on the wafer, and wherein determining the one or more parameters of the wafer inspection process is performed based on the metrology data for the wafer in combination with the metrology or inspection data for the reticle.

35. The system of claim 20, wherein the one or more parameters comprise one or more additional areas of the wafer or the other wafer used for field-to-field inspection performed within dies during the wafer inspection process.

36. The system of claim 20, wherein the computer subsystem is further configured for determining one or more parameters of a fabrication process for the wafer or the other wafer based on the metrology data, wherein the wafer inspection process is further performed on the wafer or the other wafer after the fabrication process is performed on the wafer or the other wafer, and wherein determining the one or more parameters of the water inspection process is performed based on the metrology data for the wafer in combination with the one or more parameters of the fabrication process.

37. The system of claim 20, wherein determining the one or more parameters further comprises determining one or more characteristics of noise in output generated for one or more additional areas of the wafer or the other wafer by the inspection subsystem during the wafer inspection process based on the metrology data and determining one or more parameters of output noise reduction performed during the wafer inspection process based on the one or more determined characteristics of the noise.

* * * * *